United States Patent
Wake et al.

[11] Patent Number: 6,100,520
[45] Date of Patent: Aug. 8, 2000

[54] DETECTOR ARRAY FOR USE IN A LASER IMAGING APPARATUS

[75] Inventors: Robert H. Wake, Sunrise; Richard J. Grable, Plantation, both of Fla.

[73] Assignee: Imaging Diagnostic Systems, Inc., Plantation, Fla.

[21] Appl. No.: 08/963,760

[22] Filed: Nov. 4, 1997

Related U.S. Application Data

[60] Provisional application No. 60/032,591, Nov. 29, 1996, provisional application No. 60/032,592, Nov. 29, 1996, and provisional application No. 60/032,593, Nov. 29, 1996.

[51] Int. Cl.[7] ................................ A61B 10/00; H01J 3/14
[52] U.S. Cl. .................. 250/239; 250/208.2; 250/237 R
[58] Field of Search ................................ 250/239, 237 R, 250/208.1, 208.2, 370.08, 370.01, 363.08, 363.02, 363.01, 332, 334, 330, 339.05, 339.01; 356/218, 220, 222, 225; 600/407, 425

[56] References Cited

U.S. PATENT DOCUMENTS

| | | |
|---|---|---|
| 3,684,889 | 8/1972 | Priessnetz et al. ...................... 250/239 |
| 3,973,126 | 8/1976 | Redington et al. ....................... 378/17 |
| 4,075,883 | 2/1978 | Glover ..................................... 73/607 |
| 4,515,165 | 5/1985 | Carroll . | 
| 4,767,928 | 8/1988 | Nelson et al. . |
| 4,945,239 | 7/1990 | Wist et al. . |
| 5,049,741 | 9/1991 | Fukuda et al. .......................... 250/239 |
| 5,148,022 | 9/1992 | Kawaguchi et al. . |
| 5,365,061 | 11/1994 | Enrique Munoz Elizondo ...... 250/239 |
| 5,636,637 | 6/1997 | Guiolet et al. . |
| 5,664,574 | 9/1997 | Chance . |
| 5,692,511 | 12/1997 | Grable ..................................... 600/425 |
| 5,719,398 | 2/1998 | Colak ..................................... 250/341.1 |
| 5,952,664 | 9/1999 | Wake et al. .......................... 250/459.1 |

FOREIGN PATENT DOCUMENTS 0 614 645  8/1993  European Pat. Off. .

*Primary Examiner*—John R Lee
*Attorney, Agent, or Firm*—Shlesinger, Arkwright & Garvey LLP

[57] ABSTRACT

A detector array for use in a laser imaging apparatus, comprises a plurality of housings disposed in an arc around an opening in which an object to be scanned is disposed, each housing including an open front end, a rear end and a longitudinal axis; and a detector disposed within each housing at a distance from the front end, thereby to restrict the field of view of each detector. The housings are adapted to be orbited around the object about an orbit axis. Each detector is adapted to simultaneously detect light exiting from the object within the respective field of view of each detector. A method for collecting light exiting from a object being scanned with a light source is also disclosed.

22 Claims, 4 Drawing Sheets

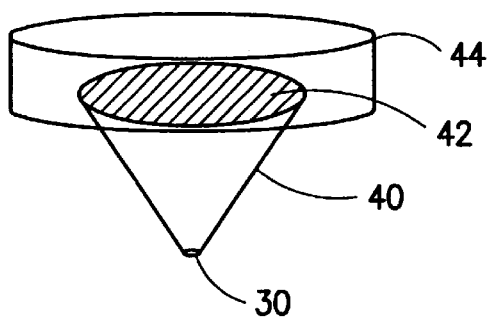
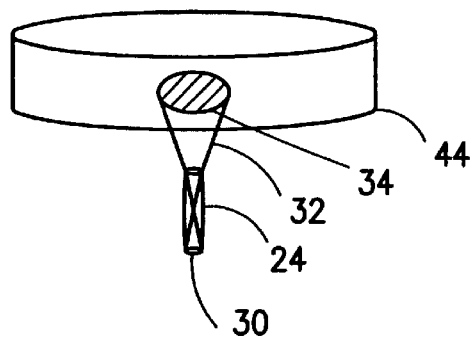
FIG. 3    FIG. 4
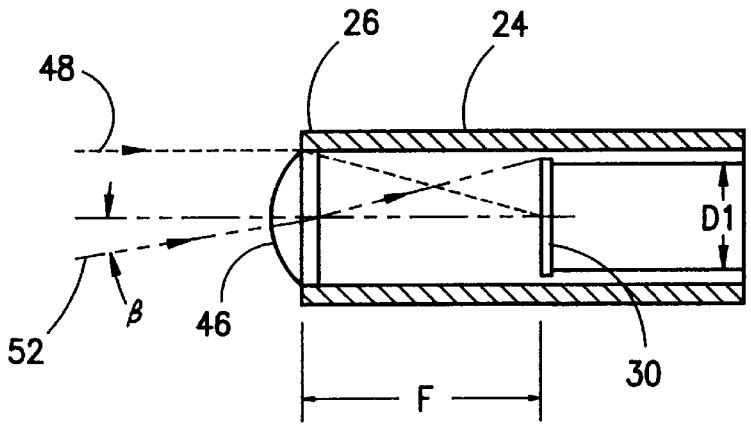
FIG. 5
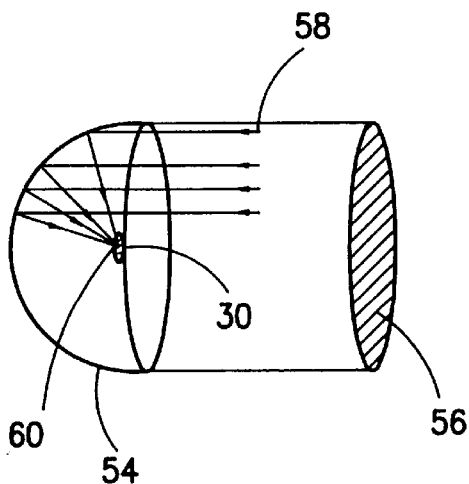
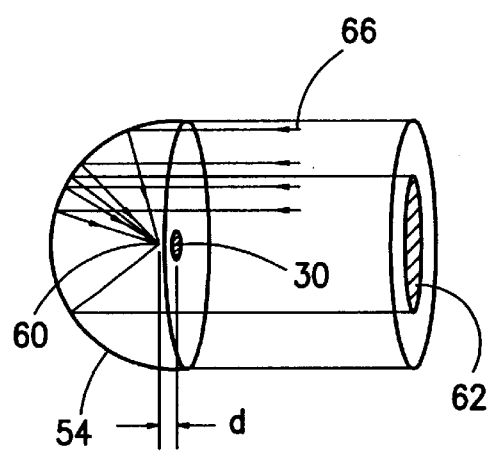
FIG. 6A    FIG. 6B

DETECTOR ARRAY FOR USE IN A LASER IMAGING APPARATUS

RELATED APPLICATIONS

This application is related to provisional applications Ser. Nos. 60/032,591, 60/032,592 and 60/032,593, all filed on Nov. 29, 1996, which are hereby incorporated by reference.

This application is also related to copending application Ser. No. 08/484,904, filed Jun. 7, 1995, now U.S. Pat. No. 5,692,511, which is hereby incorporated by reference.

FIELD OF THE INVENTION

The present invention relates generally to a diagnostic medical imaging apparatus that employs a near-infrared laser as a radiation source and a detector array with restricted fields of views directed to their own patch of surface of the object being scanned to simultaneously detect the intensity of light exiting from the object for use in image reconstruction.

BACKGROUND OF THE INVENTION

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticated, automated equipment to reliably accomplish the detection process.

The x-ray absorption density resolution of present photographic x-ray methods is insufficient to provide reliable early detection of malignant tumors. Research has indicated that the probability of metastasis increases sharply for breast tumors over 1 cm in size. Tumors of this size rarely produce sufficient contrast in a mammogram to be detectable. To produce detectable contrast in photographic mammogram 2–3 cm dimensions are required. Calcium deposits used for inferential detection of tumors in conventional mammography also appear to be associated with tumors of large size. For these reasons, photographic mammography has been relatively ineffective in the detection of this condition.

Most mammographic apparatus in use today in clinics and hospitals require breast compression techniques which are uncomfortable at best and in many cases painful to the patient. In addition, x-rays constitute ionizing radiation which injects a further risk factor into the use of mammographic techniques as most universally employed.

Ultrasound has also been suggested as in U.S. Pat. No. 4,075,883, which requires that the breast be immersed in a fluid-filled scanning chamber, U.S. Pat. No. 3,973,126 also requires that the breast be immersed in a fluid-filled chamber for an x-ray scanning technique.

In recent times, the use of light and more specifically laser light to non-invasively peer inside the body to reveal the interior structure has been investigated. This technique is called optical imaging. Optical imaging and spectroscopy are key components of optical tomography. Rapid progress over the past decade have brought optical tomography to the brink of clinical usefulness. Optical wavelength photons do not penetrate in vivo tissue in a straight line as do x-ray photons. This phenomena causes the light photons to scatter inside the tissue before the photons emerge out of the scanned sample.

Because x-ray photons propagation is essentially straight-line, relatively straight forward techniques based on the Radon transform have been devised to produce computed tomography images through use of computer algorithms. Multiple measurements are made through 360° around the scanned object. These measurements, known as projections, are used to back-project the data to create an image representative of the interior of the scanned object.

Another aspect of image reconstruction algorithm development relates to certain assumptions concerning the optical path through a scanned object starting at the point at which the radiation beam of photons initially enters the scanned object and the point on the scanned object at which the photons finally exit. The basis for the required assumptions is that there is no direct way of visualizing the actual optical path through a scanned object, in particular in vivo breast tissue, and measurements made through use of experimental models or phantoms provide empirical information of probable optical paths. Through knowledge of the physical relationship of the radiation beam, the scanned object's perimeter, and the respective sensor or sensors, reconstruction algorithm developed is possible.

In optical tomography, the process of acquiring the data that will ultimately be used for image reconstruction is the first important step. Light photon propagation is not straight-line and techniques to produce cross-sectional images are mathematically intensive. To achieve adequate spatial resolution, multiple sensors are employed to measure photon flux density at small patches on the surface of the scanned object. The volume of an average female breast results in the requirement that data must be acquired from a large number of patches. The photon beam attenuation induced by the breast tissue reduces the available photon flux to an extremely low level and requires sophisticated techniques to capture the low level signals.

Methods to acquire the scanning data are engineering issues that acquire low level signals, simultaneous data acquisition from a large number of sensors surrounding the breast, multiple levels of sensors surrounding the breast to allow rapid data acquisition, and both rotation and translation control of sensors and laser beam.

The present invention provides efficient methods for acquisition of low level photon flux signals from multiple locations around the scanned breast.

OBJECTS AND SUMMARY OF THE INVENTION

It is an object of the present invention to provide a detector array for use in a laser imaging apparatus that acquires photon intensity data by direct observation of the surface of the scanned object from various observation points with known geometry.

It is another object of the present invention to provide a detector array configured in a circle or arc around the scanned object to allow simultaneous acquisition of photon intensity data while the detector array and the radiation beam are at one fixed location.

It is still another object of the present invention to provide a detector array where each of the detectors has a restricted field of view of a surface of the scanned object.

It is another object of the present invention to provide a detector array where the fields of view of two detectors are combined to view a common area on the surface of the scanned object.

In summary, the present invention provides a detector array for use in a laser imaging apparatus, comprising a plurality of housings disposed in an arc around an opening in which an object to be scanned is disposed, each housing including an open front end, a rear end and a longitudinal axis; and a detector disposed within each housing at a distance from the front end, thereby to restrict the field of view of each detector. The housings are adapted to be orbited around the object about an orbit axis. Each detector is adapted to simultaneously detect light exiting from the object within the respective field of view of each detector. Each housing may be provided with a lens at its front end to further restrict the field of view of the detector.

A method for collecting light exiting from a object being scanned with a light source is also provided, comprising the steps of providing a source of laser beam; directing the laser beam toward the object being scanned; orbiting the laser beam around the object; providing a plurality of sensors adapted to simultaneously detect the laser beam after passing through the object; and restricting the field of view of each detector so that each detector only sees its own patch of surface of the scanned object, each patch not overlapping with adjacent patch.

These and other objects of the present invention will become apparent from the following detailed description.

BRIEF DESCRIPTIONS OF THE DRAWINGS

FIG. 3 is a schematic perspective view of a detector with unrestricted field of view looking at a patch of surface on the scanned object.

FIG. 4 is schematic perspective view of a detector assembly with a restricted field of view looking at a smaller patch of surface on a scanned object.

FIG. 5 is longitudinal cross-sectional view of a detector assembly used in the present invention.

FIG. 6A is a schematic perspective view of a paraboloidal mirror with a detector disposed at its focal point.

FIG. 6B is similar to FIG. 6A, with the detector placed at a distance from the focal point of the mirror to restrict its field of view.

DETAILED DESCRIPTION OF THE INVENTION

Figure 1:
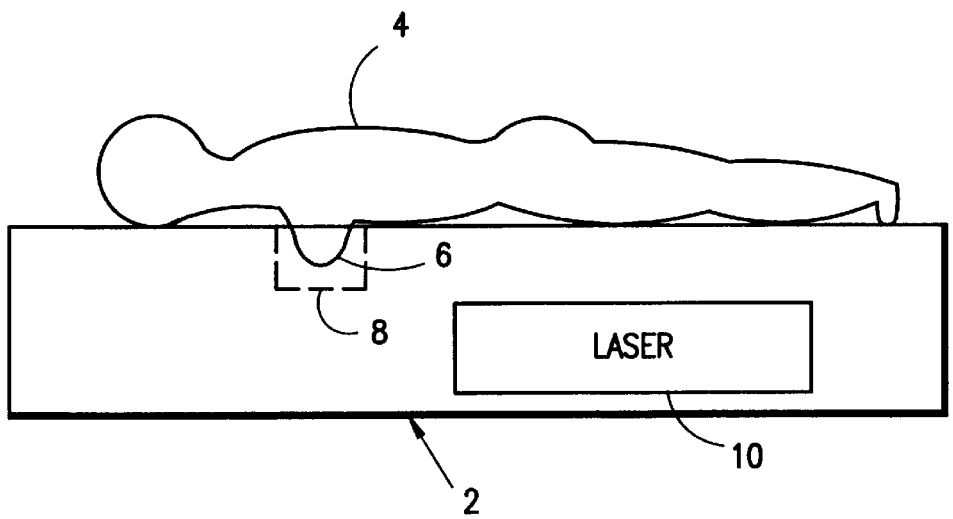
FIG. 1 is a schematic side elevational view of a scanning apparatus including a scanning chamber made in accordance with the present invention, showing a patient positioned on a support platform with her breast pendent within the scanning chamber for an optical tomographic study.

A scanning apparatus 2, such as that described in copending application Ser. No. 08/484,904, filed Jun. 7, 1995, now U.S. Pat. No. 5,692,511 is schematically disclosed in FIG. 1. A patient 4 is positioned prone on a top surface of the apparatus 2 with her breast 6 pendent within a scanning chamber 8. A laser beam from a laser source 10 is operably associated with the scanning chamber 8 to illuminate the breast 6.

Figure 2:
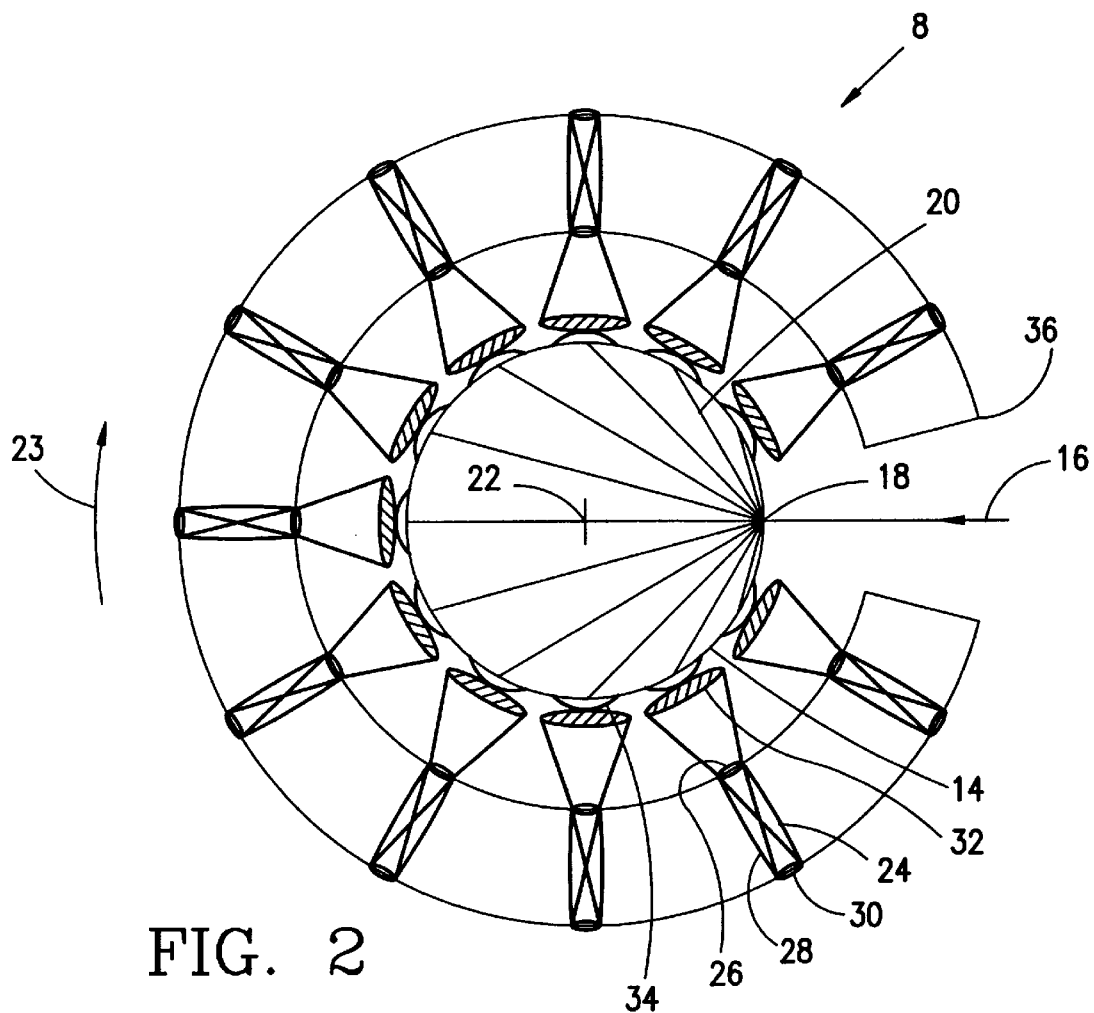
FIG. 2 is a schematic top view of the scanning chamber of FIG. 1, showing a plurality of detector assemblies with restricted fields of views disposed around an object to be scanned.

The scanning chamber 8 is shown schematically in plan view in FIG. 2. The scanning chamber includes a plurality of detector assemblies 12 disposed in an arc to define an opening in which an object 14 to be scanned is positioned. A laser beam 16 impinges the object at point 18. Light exiting from the object 18, such as the rays 20 is picked up by the respective detector assembly 12, which is then used to provide an image of the scanned object. The rays 20 are represented as chords originating from the point of entry 18 of the laser beam 16 and exiting at various points on the perimeter of the scanned object. The detector assemblies 12 are digitally orbited around the object 14 about an orbit center 22 at equal angular increments for a total angular displacement of 360°. The object is illuminated with the laser beam 16 at each angular position in the orbit 23 and light emerging from the object depicted by the chords 20 at one or more locations on the perimeter of the scanned object at one instant in time or in a period of time acquired simultaneously, is picked up by the respective detector assemblies 12. Each detector assembly has its longitudinal axis directed toward the orbit center 22. The detector assemblies 12 are secured to a support 36, which is orbited in orbit 23 around the object 14 being scanned. After each complete orbit, the array of detector assemblies 12 and the laser beam 16 are moved vertically to a new position to scan a different slice plane of the object. This is repeated until all the slice planes of the object has been scanned.

Each detector assembly 12 includes an opaque housing 24 with an open front end 26 and a rear end 28 in which a detector 30 is disposed. The housing 24 can be tubular, round, square or other cross-sectional shape. The housing 24 is designed to restrict the field of view of its respective detector 30, such that each detector is only looking at its own smaller area of the scanned object. The field of view of each detector assembly 12 is schematically indicated at 32. A patch or surface seen on the scanned object by the respective detector assembly is schematically indicated at 34.

The field of view 32 and the respective patch of surface 34 are configured such that adjacent patches of surface do not overlap each other. In this way, each detector assembly is uniquely assigned to a patch of surface at each angular position of the orbit so that light coming from one patch of surface could only be detected by the respective detector whose field of view covers that particular patch of surface. Each detector 30 is active to detect any light emerging from its respective patch of surface, since the light beam 16 can course through the object in any paths, such as those depicted by the chords 20.

The laser beam 16 may be provided by a near infrared laser, a laser diode or other near infrared sources. The detectors 30 may be photo-diodes, avalanche photo-diodes photo-transistors, PIN diodes, photo-multiplier tubes or other photo-sensitive devices.

The detector 30 without using the housing 24 would have an unrestricted view 40 on a portion of the surface 42 that can be seen on a slice plane 44 from the object being scanned, as best shown in FIG. 3. When the field of view of the detector 30 is restricted, through the use of housing 24, the surface on the slice plane 44 that can be seen by the detector is reduced to a smaller patch of surface 34, as best shown in FIG. 4. By restricting the field of view of each detector the surface viewed by each detector will not overlap with the other viewed surfaces, thereby providing accuracy to the data provided by each detector.

The open front end 26 of each housing 24 may be provided with a lens 46 to further restrict the field of view of the detector 30, as best shown in FIG. 5. The focal length F of the lens 46 and the diameter D1 of the detector 30 combine to restrict the field of view as described by the following equation, $$\beta = \frac{1}{2} \text{ field of view}$$
$$= (D1)^2/(2*F) \text{ radians} \qquad (1)$$

Parallel ray 48 converges to indicate the position of the focal point on the detector 30. The non-parallel ray 52 at or less than the acceptance angle β will pass through the lens 46 and is directed to the detector 30. Rays having an angle greater than the acceptance angle β will not reach the detector 30.

The numerical aperture controls the angle of light accepted by the lens 46. As the F-number of the lens increases, the acceptance angle decreases and the field of view becomes narrower. The F-number of the lens is defined as, $$F\text{-number}=F/D1. \qquad (2)$$

The numerical aperture of a lens is defined as, $$\text{Numerical Aperture}=0.5/F\text{-number}. \qquad (3)$$

When the focal length F of the lens 46 increases, the acceptance angle β decreases. Any non-parallel rays outside the acceptance angle β will miss the detector 30. A lower acceptance angle β further restricts the field of view of the detector 30. Other lens combinations may be made to restrict the field of view of the detector 30.

Another way of restricting the field of view of the detector 30 is disclosed in FIGS. 6A and 6B. A paraboloidal mirror 54 with a field of view 56. Parallel rays 58 converge on the focus point 60. The detector 30 placed at the focus point 60 will receive the parallel rays 58 within the field of view 56. To restrict the field of view of the mirror 54 to a smaller area 62, the detector 30 is displaced at distance d away from the focus point 60, as best shown in FIG. 6B. Rays 66 that are outside of the field of view 62 are seen to miss the detector 30. Other mirror combinations are possible that would result in similar field of view restriction.

Knowledge of the restricted field of view 32 of the detectors 30, the physical position of the detectors assemblies in the array relative to the axis of the orbit of rotation, the paths of the photons within the scanned object as represented by the chords 20 and knowledge of the photons emerging from the scanned object at one or more locations on the perimeter of the scanned object at one instant in time or in a period of time acquired simultaneously, provide information for image reconstruction.

Figure 7:
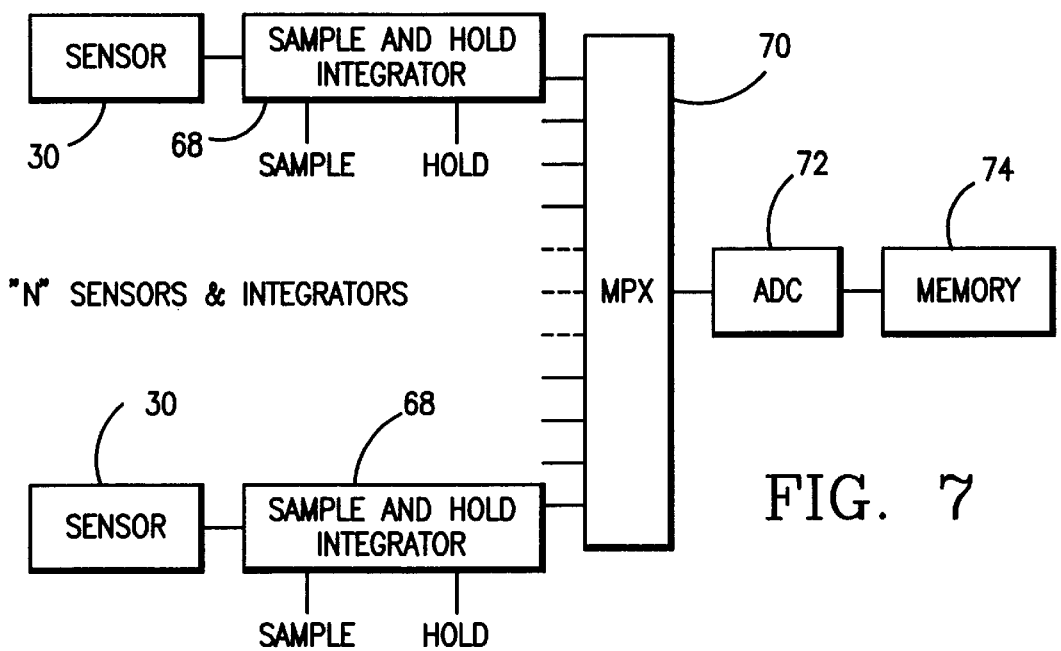
FIG. 7 is a block diagram of a circuit used in the present invention to acquire data simultaneously from the detector array.

A circuit for acquiring data for one or more of the detectors 30 is disclosed in FIG. 7. Each detector 30 is coupled to a sample and hold integrator 68. During the sample interval, a signal is developed by the integrator 68 as a function of the photons striking the detector 30. During the hold interval, the detector input is terminated and the integrated signal level is held at the level it reached during the sample interval. A multiplexer 70 is used to connect the respective integrator outputs to an analog to digital converter 72. The digitized individual detector or sensor response is stored in memory 74 for later use in image reconstruction. The circuit allows for simultaneous acquisition of data from all the detectors 30. The circuit in image reconstruction are described in provisional applications Ser. Nos. 60/032,590 and 60/032,594 both filed on Nov. 29, 1996, which are hereby incorporated by reference. Determination of the boundary perimeter of the scanned object is disclosed in provisional applications Ser. Nos. 60/029,897 and 60/029,898, both filed Nov. 8, 1996, which are hereby incorporated by reference.

Figure 8:
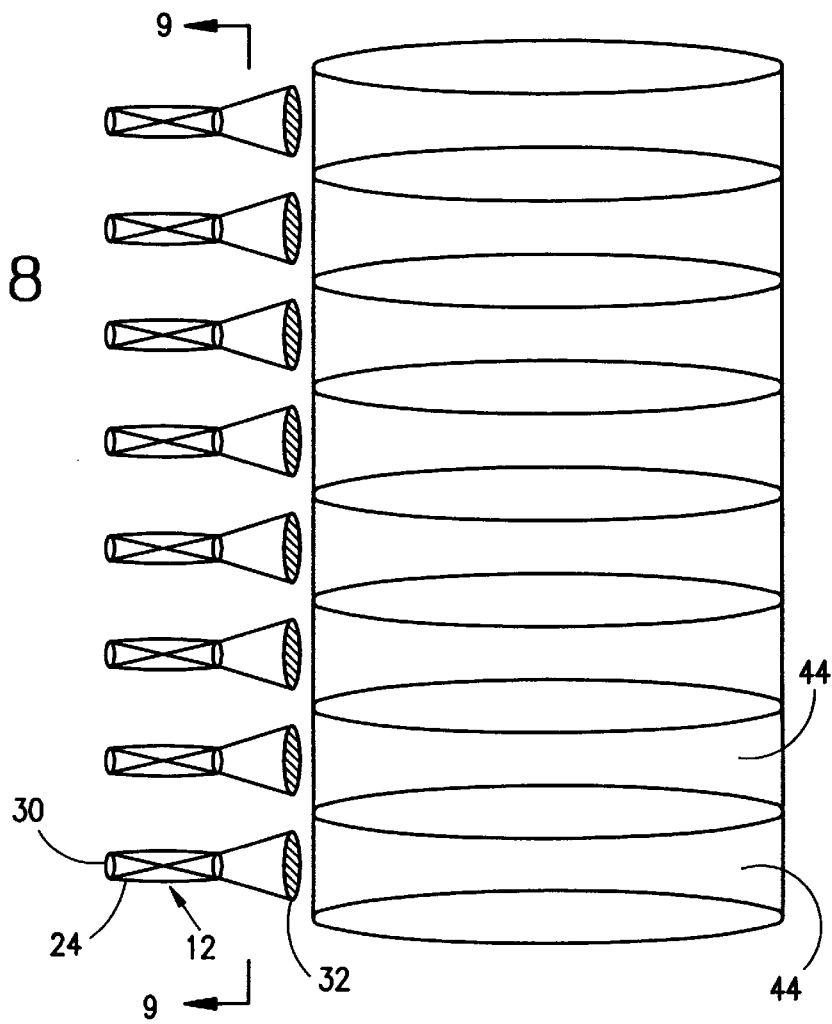
FIG. 8 is a schematic perspective view of a 2-dimensional detector array, using a number of 1-dimensional arrays of FIG. 2 stacked vertically.
Figure 9:
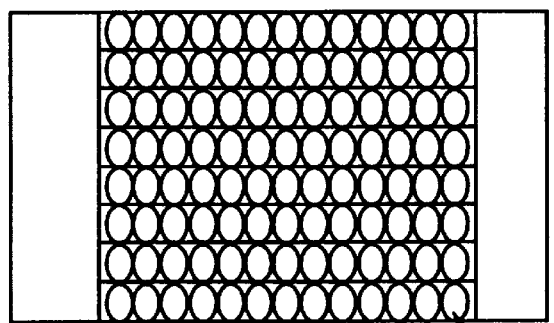
FIG. 9 is a cross-sectional view along line 9—9 of FIG. 8.

The detector assemblies 12 may be arranged in a 2-dimensional array, where the detector assemblies are arrayed horizontally and vertically, as best shown in FIGS. 8 and 9. The object being scanned is divided into contiguous slice planes 44. The 2-dimensional array is configured to simultaneously acquire data from the contiguous slice planes 76 within the scanned object. The simultaneous acquisition of data significantly reduces the time required to scan the entire object. The acquired data is then used to reconstruct either single slice planes or 3-dimensional reconstruction of the scanned object, taking advantage of ray paths that cross slice planes.

Figure 10:
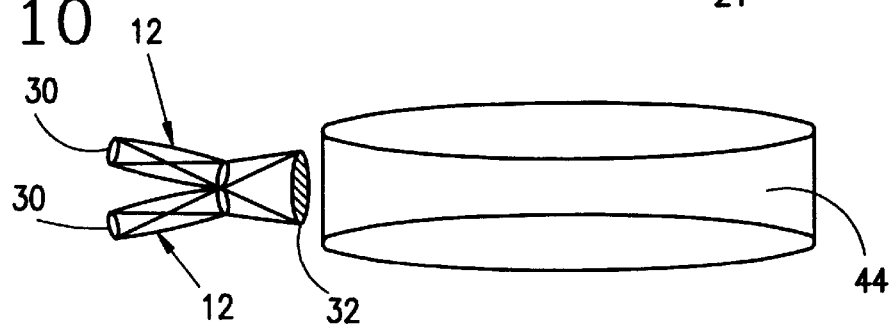
FIG. 10 is a schematic perspective view showing two detector assemblies with their fields of views combined to view a common area on the surface of the scanned object.
Figure 11:
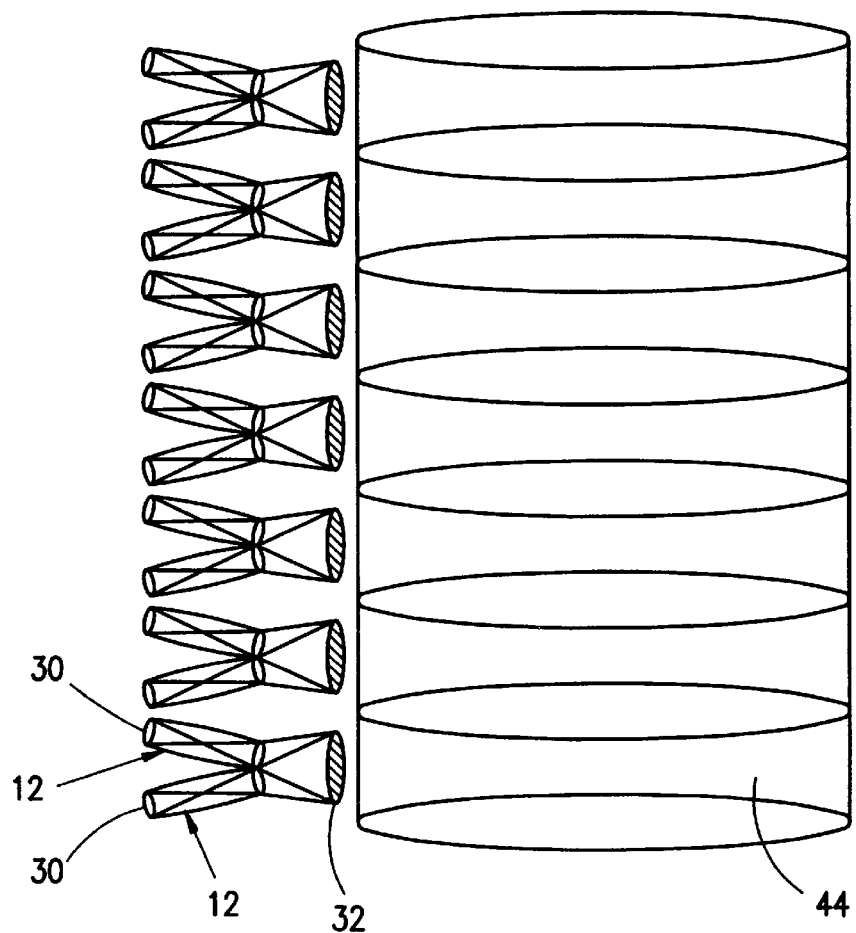
FIG. 11 is a schematic perspective view of the detector assemblies of FIG. 10 arranged vertically to form a two-dimensional detector array similar to FIG. 8.

Two detector assemblies 12 may be combined to share a common field of view on the patch of surface of the scanned object. The use of two detectors 30 significantly increases the number of photons that can be seen radiating from the respective patch of surface of the scanned object, as best shown in FIG. 10. The doubled-up detectors assemblies, in addition to being arrayed horizontally, may also be arranged vertically to form a 2-dimensional configuration to create a "wall" of detectors, as best shown in FIG. 11. The arrangement is used to simultaneously acquire data from contiguously slice planes within a scanned object. The acquired data can be used to reconstruct either a single slice image or a 3-dimensional reconstruction of the scanned object.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A detector array for use in a laser imaging apparatus, comprising:

a) a plurality of housings disposed in an arc around an opening in which an object to be scanned is disposed, each housing including an open front end directed to the object, a rear end and a longitudinal axis;

b) a plurality of detectors each being operably associated with a respective housing at a distance from said front end, thereby to restrict the field of view of each detector;

c) said housings being adapted to be orbited around the object about an orbit axis; and d) each of said detectors being adapted to simultaneously detect light exiting from the object within the respective field of view of each detector.

2. A detector array as in claim 1, wherein:

a) each housing longitudinal axis is disposed toward said orbit axis.

3. A detector array as in claim 1, wherein:

a) each housing is tubular.

4. A detector array as in claim 1, wherein:
a) each housing is round in cross-section.

5. A detector array as in claim 1, wherein:
a) each housing is square in cross-section.

6. A detector array as in claim 1, and further comprising:
a) a lens disposed at each front end of said housings for restricting the field of view of each detector.

7. A detector array as in claim 6, wherein:
a) said lens is plano-convex.

8. A detector array as in claim 1, wherein:
a) said housings are disposed in a one-dimensional array.

9. A detector array as in claim 1, wherein:
a) said housings are disposed in a two-dimensional array.

10. A detector array as in claim 1, wherein:
a) at least two housings are directed toward the object being scanned such that their field of views merge together.

11. A detector array as in claim 1, and further comprising:
a) a sample and hold integrator connected to each detector.

12. A detector array as in claim 1, wherein:
a) each of said detectors is disposed within respective housing.

13. A detector array for use in a laser imaging apparatus, comprising:
a) a plurality of housings disposed in an arc around an opening in which an object to be scanned is disposed, each housing including an open front end directed to the object, a rear end and a longitudinal axis;
b) a plurality of detectors each being operably associated with a respective housing at a distance from said front end to restrict the field of view of each detector so that each detector sees only its own patch of surface of the scanned object, each patch not overlapping with an adjacent patch; and
c) said housings being adapted to be orbited around the object about an orbit axis.

14. A detector array as in claim 13, wherein:
a) each of said detectors is disposed within respective housing.

15. A detector array as in claim 13, wherein:
a) each housing is tubular.

16. A detector array as in claim 13, wherein:
a) each housing is round in cross-section.

17. A detector array as in claim 13, wherein:
a) each housing is square in cross-section.

18. A detector array as in claim 13, and further comprising:
a) a lens disposed at each front end of said housings for restricting the field of view of each detector.

19. A detector array as in claim 18, wherein:
a) said lens is plano-convex.

20. A detector array as in claim 13, wherein:
a) said housings are disposed in a one-dimensional array.

21. A detector array as in claim 13, wherein:
a) said housings are disposed in a two-dimensional array.

22. A detector array as in claim 13, wherein:
a) at least two housings are directed toward the object being scanned such that their field of views merge together.

* * * * *